US005605822A

United States Patent [19]
Emerson et al.

[11] Patent Number: 5,605,822
[45] Date of Patent: Feb. 25, 1997

[54] METHODS, COMPOSITIONS AND DEVICES FOR GROWING HUMAN HEMATOPOIETIC CELLS

[75] Inventors: Stephen G. Emerson; Michael F. Clarke; Bernhard O. Palsson, all of Ann Arbor, Mich.

[73] Assignee: The Regents of The University of Michigan, Ann Arbor, Mich.

[21] Appl. No.: 352,196

[22] Filed: Dec. 1, 1994

Related U.S. Application Data

[63] Continuation of Ser. No. 100,337, Jul. 30, 1993, abandoned, which is a continuation of Ser. No. 628,343, Dec. 17, 1990, abandoned, which is a continuation-in-part of Ser. No. 366,639, filed as PCT/US90/03438, Jun. 14, 1990, abandoned.

[51] Int. Cl.$^6$ ............... C12N 15/00; C12N 5/00; C12M 3/00
[52] U.S. Cl. ............... 435/172.3; 435/172.1; 435/204.1; 435/373; 435/377; 435/395; 435/401
[58] Field of Search ............... 435/172.3, 240.1, 435/240.2, 240.23, 240.241, 204, 285, 286

[56] References Cited

U.S. PATENT DOCUMENTS

| | | |
|---|---|---|
| 4,135,975 | 1/1979 | Lichtman et al. . |
| 4,481,946 | 11/1984 | Altshuler et al. . |
| 4,486,188 | 12/1984 | Altshuler et al. . |
| 4,514,499 | 4/1985 | Noll . |
| 4,714,680 | 12/1987 | Civin . |
| 4,808,611 | 2/1989 | Cosman . |
| 4,810,643 | 3/1989 | Souza . |
| 4,847,201 | 7/1989 | Kawasaki et al. . |
| 4,861,714 | 8/1989 | Dean et al. . |
| 4,889,812 | 12/1989 | Guinn et al. . |
| 4,963,489 | 10/1990 | Naughton ............... 435/240.1 |
| 4,965,204 | 10/1990 | Civin . |
| 5,004,681 | 4/1991 | Boyse et al. . |
| 5,032,407 | 7/1991 | Wagner et al. . |
| 5,032,508 | 7/1991 | Naughton et al. . |
| 5,061,620 | 10/1991 | Tsukamoto et al. . |
| 5,199,942 | 4/1993 | Gillis . |

FOREIGN PATENT DOCUMENTS

| | | |
|---|---|---|
| 2062741 | 12/1990 | Canada . |
| 0358506 | 3/1990 | European Pat. Off. . |
| 0455482 | 11/1991 | European Pat. Off. . |
| WO93/18136 | 9/1993 | European Pat. Off. . |
| WO93/18137 | 9/1993 | European Pat. Off. . |
| WO95/06409 | 3/1995 | WIPO . |

OTHER PUBLICATIONS

Ventura et al (Experimental Hematology 1990, 18, 878–82).
Krumwieh et al (International Journal of Cell Cloning 1990, 8, Supplement 1, 229–48).
Heyworth et al (Growth Factors 1990, 2, 197–211).
A. Mizrahi, Process Biochemistry, (Aug. 1986) pp. 108–112 "Production of Biologicals from Animal Cells –An Overview".
Adamson et al., Canadian Jour. Of Chem. Eng., vol. 64 (Aug. 1986) pp. 531–539 "Industrial Mammalian Cell Culture".
T. M. Dexter et al., Long–Term Bone Marrow Culture, (1984) pp. 57–96.
Caldwell et al J. Cell Phys. 147:344. 1991.
Jordan et al Immunogenetics 18:165. 1983.
Hock et al Nature 309:275. 1986.
Freshney Culture of Animal Cells, pp. 305–307. 1987.
Wang et al Science 228:810. 1985.
Glachen et al Trends in Biotech 1(4): 102. 1983.
Yang et al Cell 47:3. 1986.
"Expansion of Human Bone Marrow Progenitor Cells in High Cell Density Continuous Perfusion System"; Bernhard O. Palsson, et al; *Bio/Technology*, vol. 11, Mar. 1993; pp. 368–372.
"Characterization and Partial Purification of Human Marrow Cells Capable of Initiating Long–Term Hematopoiesis In Vitro"; Heather J. Sutherland, et al; *Blood*; vol. 74, No. 5, Oct., 1989; pp. 1563–1570.
"Expansion of Primitive Human Hematopoietic Progenitors in a Perfusion Bioreactor System with IL–3, IL–6, and Stem Cell Factor"; Manfred R. Koller, et al; *Bio/Technology*, vol. 11; Mar., 1993; pp. 358–363.
"Functional Characterization of Individual Human Hematopoietic Stem Cells Cultured at Limiting Dilution of Supportive Marrow Stromal Layers"; Heather J. Sutherland, et al; *Proc. Natl. Acad. Sci. USA*; vol. 87, May, 1990; pp. 3584–3588.
"The Human Hematopoietic Stem Cell in Vitro and In Vivo"; C. J. Eaves, et al; *Blood Cells*; 18; 1992; pp. 301–307.
"Alternative Mechanisms With and Without Steel Factor Support Primitive Human Hematopoiesis"; H. J. Sutherland, et al; *Blood*; vol. 81, No. 6, Mar. 15, 1993; pp. 1464–1470.
"Human Recombinant Granulocyte–Macrophage Colony–Stimulating Factor: A Multilineage Hematopoietin"; Colin A. Sieff, et al; *Science*, vol. 230; Dec., 1985; pp. 1171–1173.

(List continued on next page.)

*Primary Examiner*—Suzanne E. Ziska
*Attorney, Agent, or Firm*—Oblon, Spivak, McClelland, Maier & Neustadt, P.C.

[57] ABSTRACT

Methods, compositions and devices are provided for the growth of hematopoietic cells in culture. Bioreactors are provided in which diverse cell types are simultaneously cultured in the presence of appropriate levels of nutrients and growth factors substantially continuously maintained in the bioreactor while removing undesirable metabolic products. This simultaneous culture of multiple cell types is required for the successful reconstruction of hematopoietic tissue ex vivo. At least one growth factor is provided through excretion by transfected stromal cells, particularly heterologous cells. Means are provided for maintaining the stromal cells and hematopoietic cells separately, to allow for early removal of the hematopoietic cells.

64 Claims, 4 Drawing Sheets

OTHER PUBLICATIONS

"Use of Limiting–Dilution Type Long–Term Marrow Cultures in Frequency Analysis of Marrow–Repopulating and Spleen Colony–Forming Hematopoietic Stem Cells in the Mouse"; Rob E. Ploemacher, et al; *Blood*, vol. 78, No. 10; Nov. 15, 1991; pp. 2527–2533.

"Evaluation of Hematopoiesis in Long–Term Bone Marrow Culture: Comparison of Species Differences"; C. E. Eastment, et al; *Long–Term Bone Marrow Culture*; 1984; pp. 97–118.

"Bone Marrow Stromal Fibroblasts Secrete Interleukin–6 and Granulocyte–Macrophage Colony–Stimulating Factor in the Absence of Inflammatory Stimulation: Demonstration by Serum–Free Bioassay, Enzyme–Linked Immunosorbent Assay, and Reverse Transcriptase Polymerase Chain Reaction"; Susan C. Guba, et al; *Blood*, vol. 80, No. 5; Sep. 1, 1992; pp. 1190–1198.

"Formation of haematopoietic microenvironment and haematopoietic stem cells from single human bone marrow stem cells"; Shiang Huang, et al; *Nature*, vol. 360; Dec. 24–31, 1992; pp. 745–749.

"Primitive hemopoietic stem cells: direct assay of most productive populations by competitive repopulation with simple binomial, correlation and covariance calculations"; David E. Harrison, et al; *Experimental Hematology*, 21; 1993; pp. 206–219.

"Methodology of Long–Term Culture of Human Hematopoietic Cells"; Connie J. Eaves, et al; *J. Tiss. Cult. Meth.*, 13; 1991; pp. 66–62.

"Expression of Human Adenosine Deaminase in Nonhuman Primates After Retrovirus–Mediated Gene Transfer"; Philip W. Kantoff, et al; *J. Exp. Med.*, vol. 166; Jul., 1987; pp. 219–234.

"Mitogenic Effect of Bestatin on Lymphocytes"; Masaaki Ishizuka, et al; *The Journal of Antibiotics*, vol. XXXIII, No. 6; Jun., 1980; pp. 653–662.

"In Vitro Growth of Murine T Cells, II. Growth of in Vitro Sensitized Cells Cytotoxic for Alloantigens"; Steven A. Rosenberg, et al.; *The Journal of immunology*, vol. 121, No. 5; Nov., 1978; pp. 1951–1955.

"Prospects for Human Gene Therapy"; W. French Anderson; *Science*, vol. 226; Oct., 1984; pp. 401–409.

"Beneficial Effects of Reduced Oxygen Tension and Perfusion in Long–Term Hematopoietic Cultures"; Manfed R Koller, et al; *Biochemical Engineering VII*, vol. 665 of the Annals of the New York Academy of Sciences; Oct. 13, 1992; pp. 105–116.

"Recent Modifications of Technique in Human Long–Term Bone Marrow Cultures"; Joel S. Greenberger; *Long–Term Bone Marrow Culture*; 1984; pp. 119–131.

"The Message in the Medium"; T. M. Dexter; *Nature*, vol. 309, No. 28; Jun., 1984; pp. 746–747.

"Long–term culture of human bone marrow cells"; Suzanne Gartner, et al; *Proc. Natl. Acad. Sci. USA*, vol. 77, No. 8; Aug., 1980; pp. 4756–4759.

"Granuloerythropoietic Colonies in Human Bone Marrow, Peripheral Blood, and Cord Blood"; A. A. Fauser, et al; *Blood*, vol. 52, No. 6; Dec., 1978; pp. 1243–1248.

"Induction of Colonies of Hemoglobin–Synthesizing Cells by Erythropoietin In Vitro"; John R. Stephenson, et al; *Proc. Nat. Acad. Sci. USA*, vol. 68, No. 7; Jul., 1971; pp. 1542–1546.

"Retrovirus–mediated transfer and expression of drug resistance genes in human haematopoietic progenitor cells"; Randy A. Hock, et al; *Nature*, vol. 230; Mar. 20, 1986; pp. 275–277.

"Canine Model for Gene Therapy: Inefficient Gene Expression in Dogs Reconstituted With Autologous Marrow Infected With Retroviral Vectors"; Richard B. Stead, et al; *Blood*, vol. 71, No. 3; Mar., 1988; pp. 742–747.

"The Basic Science of Gene Therapy"; Richard C. Mulligan; *Science*, vol. 260; May 14, 1993; pp. 926–932.

"Human IL–3 (Multi–CSF): Identification by Expression Cloning of a Novel Hematopoietic Growth Factor Related to Murine IL–3"; Yu–Chung Yang, et al; *Cell*, vol. 47; Oct. 10, 1986; pp. 3–10.

"A Cell Culture Model for T Lymphocyte Clonal Anergy"; Ronald H. Schwartz; *Science*, vol. 248; Jun. 15, 1990; pp. 1349–1356.

"Mammalian cell culture; engineering principles and scale–up"; M. W. Glacken, et al; *Trends in Biotechnology*, vol. 1, No. 4; 1983; pp. 102–108.

"Reduced Oxygen Tension Increases Hematopoiesis in Long–term Culture of Human Stem and Progenitor Cells from Cord Blood and Bone Marrow"; Manfred R. Koller, et al; *Experimental Hematology*, 20; 1992; pp. 264–270.

"Effects of Synergistic Cytokine Combinations, Low Oxygen, and Irradiated Stroma on the Expansion of Human Cord Blood Progenitors"; Manfred R. Koller, et al; *Blood*, vol. 80, No. 2; Jul. 15, 1992; pp. 403–411.

Gail K. Naughton, et al.; Journal of Cellular Biochemistry; Hematopoeisis on Nylon Mesh Microenvironments; 19th Annual Meeting (1990).

Jerry Caldwell, et al.; Biotechnology Progress; Influence of Medium Exchange Schedules on Metabolic, Growth, and GM–CSF Secretion Rates of Genetically Engineered NIH–3T3 Cells; vol. 7; pp. 1–8; (1991).

Jerry Caldwell, et al.; Journal of Cellular Physiology; Culture Perfusion Schedules Influence the Metabolic Activity and Granulocyte–Macrophage Colony–Stimulating Factor Production Rates of Human Bone Marrow Stromal Cells; vol. 147, No. 2; pp. 344–353; (1991).

Richard M. Schwartz, et al.; Blood; In Vitro Myelopoiesis Stimulated by Rapid Medium Exchange and Supplementation with Hematopoietic Growth Factors; vol. 78, No. 12; pp. 3155–3161; (1991).

Richard M. Schwartz, et al.; Proceedings of the National Academy of Sciences; Rapid Medium Perfusion Rate Significantly Increases the Productivity and Longevity of Human Bone Marrow Cultures;; vol. 88, No. 15; pp. 6760–6764; (1991).

Krumweih et al (Behring Instituten Mitteleitung 1988, 83, 250–7).

Saeland et al (Blood 1989, 73(5), 1195–1201).

Migliaccio et al (Blood 1988, 72(1), 248–56).

Takaue et al (Blood 1990, 76, 330–35).

Coutinho et al (Blood 1990, 75, 2118–29).

Donahue et al (Science 1988, 241, 1820).

Ogawa (Hematopoietic Growth Factors 1989, 3, 453–464).

Schneider et al (Journal of Immunological Methods 1990, 129, 251–68).

Aiken et al (Journal of Pediatric Surgery 1990, 25, 140–5).

Parsons et al (Journal of Pharmacological Methods 1982, 8, 73–89).

Ehrlich et al (In Vitro 1978, 14, 443–50).

McNiece et al (Blood 1989, 73(4), 919–23).

Brandt et al (Advances in Experimental Medicine and Biology 1988, 241, 165–73).
Takaue et al (Blood 1987, 70(5), 1611–8).
Baines et al (Experimental Hematology 1988, 16, 785–9).
Podolak–Dawidziak (Haematologia 1990, 23, 121–23).
Borinaga et al (British Journal of Haematology 1990, 76, 476–83).
Favre et al (Blood 1990, 75(1), 67–73).
Myers et al (Blood 1984, 64(1), 152–5).
Gabrilove et al (Proceedings of the National Academy of Sciences USA 1986, 83, 2478–82).
Morioka et al (Research in Experimental Medicine 1990, 190, 229–38).
Hughes et al (Research in Experimental Medicine 1990, 190, 229–38).
Nolta et al (Human Gene Therapy 1990, 1, 257–68).
Caldwell et al (J. Cell. Physiol. 1991, 147, 344–353).
Caldwell et al (Biotech Progress 1991, 7, 1–8).
Lu et al (British Journal of Hematology 1988, 70:149–156).
Greenberger (Hematopoiesis, Edited by David W. Golde, Churchill Livingstone, 1984, 203–42).
Dexter et al (Long Term Bone Culture, Editors: Wright and Greenberger, 1984, Allan R. Liss, Inc. 57–96).
Adamson et al (Canadian Journal of Chemical Engineering, 1986, 64, 531–39).
Sardonini et al (Abstracts from American Institute of Chemical Engineers, Nov. 17–22, 1991, Abstract No. 259e).
Hubbell et al (Biotechnology 1991, 9, 568–572).
Feder et al (Scientific America, 1983, 248, 36–43).
Varma et al (Exp. Hematol. 1992, 20, 87–91).
Emerson et al (J. Cell. Biochem, 1991, 45, 268–71).
Mueller (Folia Hematol., 1989, 116, 731–43).
Schwartz (Doctoral Thesis in the University of Michigan, 1991) (in abstract).

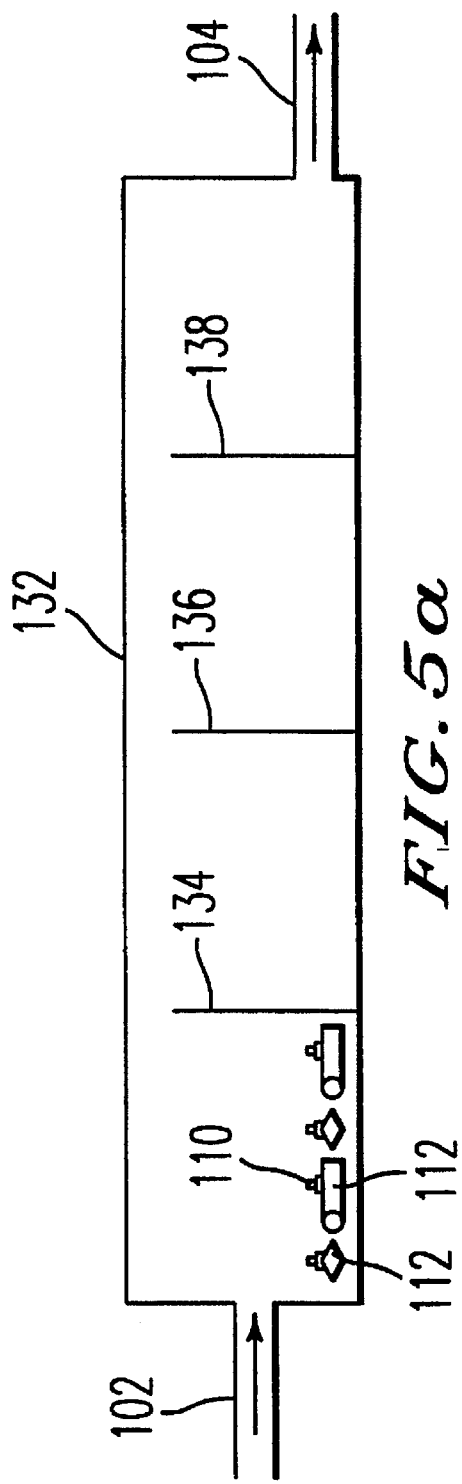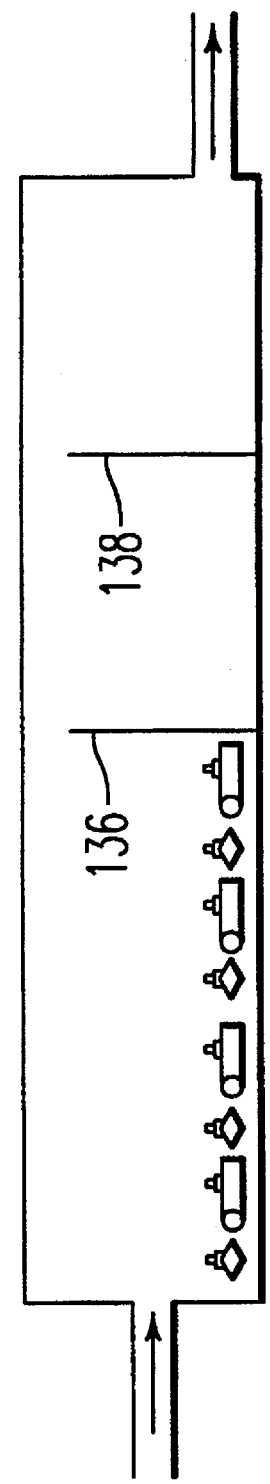

METHODS, COMPOSITIONS AND DEVICES FOR GROWING HUMAN HEMATOPOIETIC CELLS

CROSS-REFERENCE TO RELATED APPLICATIONS

This application is a continuation of application Ser. No. 08/100,337, filed on Jul. 30, 1993, now abandoned, which was a continuation of application Ser. No. 07/628,343, filed Dec. 17, 1990, now abandoned, which was a continuation-in-part of application Ser. No. 07/366,639, filed Jun. 15, 1989, now abandoned, which was filed as International Application No. PCT/US90/03438, on Jun. 14, 1990.

TECHNICAL FIELD

The field of the invention is the growth of normal mammalian cells in culture.

BACKGROUND

There is significant interest in the ability to use cells for a wide variety of therapeutic purposes. The hematopoietic system exemplifies the extraordinary range of cells involved in protection of mammalian hosts from pathogens, toxins, neoplastic cells, and other diseases. The hematopoietic system is believed to evolve from a single stem cell, from which all the lineages of the hematopoietic system derive. The particular manner in which the stem cell proliferates and differentiates to become determined in its lineage is not completely understood, nor are the factors defined. However, once the stem cell has become dedicated to a particular lineage, there appear to be a number of factors, for example colony stimulating factors, which allow, and may direct the stem cell to a particular mature cell lineage.

There are many uses for blood cells. Platelets find use in protection against hemorrhaging, as well as a source of platelet derived growth factor. Red blood cells can find use in transfusions to support the transport of oxygen. Specific lymphocytes may find application in the treatment of various diseases, where the lymphocyte is specifically sensitized to an epitope of an antigen. Stem cells may be used for genetic therapy as well as for rescue from high dose cancer chemotherapy. These and many other purposes may be contemplated.

In order to provide these cells, it will be necessary to provide a means, whereby cells can be grown in culture and result in the desired mature cell, either prior to or after administration to a mammalian host. The hematopoietic cells are known to grow and mature to varying degrees in bone, as part of the bone marrow. It therefore becomes of interest to recreate a system which provides substantially the same environment as is encountered in the bone marrow, as well as being able to direct these cells which are grown in culture to a specific lineage.

Relevant Literature

U.S. Pat. No. 4,721,096 describes a 3-dimensional system involving stromal cells for the growth of hematopoietic cells. See also references cited therein. Glanville, et al., *Nature* 292:267–269, (1981), describe the mouse metallothionein-I gene. Wong et al., *Science* 228:810–815, (1985), describe human GM-CSF. Lemischka, et al., *Cell* 45:917–927, (1986), describe retrovirus-mediated gene transfer as a marker for hematopoietic stem cells and the tracking of the fate of these cells after transplantation. Yang, et al., *Cell* 47:3–10, (1986), describe human IL-3. Chen and Okayama, *Mol. Cell. Biol.* 7:2745–2752, (1987), describe transformation of mammalian cells by plasmid DNA. Greaves, et al., *Cell* 56:979–986, (1989), describe the human CD2 gene. Civin C., Strauss L. C., Brovall C., Fackler M. J., Schwartz J. R., Shaper J. H., *J. Immunol.* 133:1576–165, (1984), describe the CD34 antigen. Martin FH, Suggs SV, Langley KE, et al., *Cell* 63:203–211, (1990), describe human S-CSF; Forrester, JV, Lackie JM, *J. Cell Science*, 70:93–110, (1984), discuss parallel flow chamber. Coulombel, L. et al., *J. Clin. Invest.*, Vol. 75:961 (1986), describe the loss of CML cells in static cultures.

SUMMARY OF THE INVENTION

Methods are provided employing reactors and compositions which allow for the efficient proliferation of hematopoietic cells in culture, particularly cells at an early stage in maturation, including stem cells. The methods employ stromal cells, normally transformed, which provide constitutive or inducible production of growth factors, which cells are physically separated to allow for easy separation of hematopoietic cells. By providing for continuous perfusion, and recycling of cells as appropriate, high densities and yields of viable hematopoietic cells may be achieved. The reactor employs a protein surface for the stromal cells and either the surface or other barrier for maintaining separation of stromal cells and hematopoietic cells.

BRIEF DESCRIPTION OF THE FIGURES

FIG. 3b is a side view of the flow chamber of FIG. 3a;

FIGS. 5a and 5b are views of a flow chamber in which barriers are removed sequentially allowing the continued growth of stromal cells.

DESCRIPTION OF THE SPECIFIC EMBODIMENTS

Figure 1:
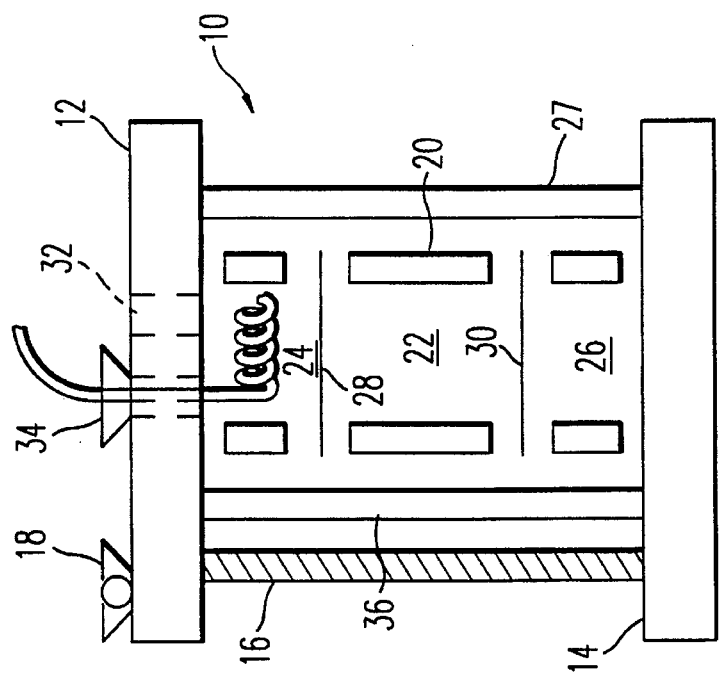
FIG. 1 is a schematic view of a perfusion chamber.

Methods are provided for the growth of hematopoietic cells in culture, employing fibroblast cells, normally transformed, for providing growth factors, with proteinaceous components added to the mixtures of the fibroblast cells and hematopoietic cells, and substantially continuous perfusion, optionally with recycling, to maintain an effective growth environment.

The description of the method therefore may be divided into descriptions of the perfusion conditions, the reactor and its internal structure, and the transformed fibroblasts.

The reactor comprises a vessel which may be of any convenient shape which allows for the necessary cell distribution, introduction of nutrients and oxygen, removal of waste metabolic products, optional recycling of hematopoietic cells, substitution of stromal cells, and harvesting of hematopoietic cells. The reactor should provide for conditions which substantially mimic bone perfusion. In vivo, about 0.08 ml of serum per ml of bone marrow per minute is perfused. This translates into about 0.3 ml of serum per $10^6$ cells per day. The media will therefore be changed on the average at least 50%, preferably at least 100%, in any 24 hour period, so as to maintain a level of metabolic products which is not growth limiting. The rate of change will generally be from about 0.5 to 1.0 ml of perfusion medium per $10^6$ cells per day, empirically mimicking in vivo perfusion rates.

The rate of perfusion in the bioreactor will vary depending on the cell density in the reactor. For cells cultured at $2-10\times10^6$ cells/ml, this rate is 1 ml/ml reactor volume per 24–48 hours, where the medium used contains 20% serum, either 10% fetal calf serum and 10% horse serum, or 20% fetal calf serum. For higher cell densities, the perfusion rate will be increased proportionately to achieve a constant serum flux per cell per time. Thus if the cells are cultured at $5\times10^8$ cell/ml the perfusion rate will be 0.1 ml/ml reactor volume per minute. These flow rates, matching serum and medium flux rates to cell density, are essential to stimulating the endogenous production of hematopoietic growth factors from the normal human bone marrow stromal cells in the culture. The hematopoietic growth factors induced by these serum and medium flux rates include GM-CSF, and may also include S-CSF, IL-6 and G-CSF as well as other hematopoietic growth factors. These rates will be established in the bioreactors such that the shear stress from longitudinal flow experienced by the stem cells and progenitor cells at their stromal cell attachment sites are between 1.0 and 5.0 dynes/square cm.

Various media may be employed for the growth of hematopoietic and stromal cells. Illustrative media include MEM, IMDM, and RPMI, which may be supplemented by combinations of 5–20% fetal calf serum, 5–20% calf serum, and 0–15% horse serum, and/or serum free media supplemented with PDGF, EGF, FGF, HGF or other growth factors to stimulate stromal cells or stem cells. To supplement the growth factors provided by the transformed fibroblasts, additional growth factors may be included in the perfusion medium, particularly where dedicated cells of a particular lineage are desired. Among the growth factors which may be included in the perfusion medium, either by stromal cell secretion or addition, are GM-CSF, G-CSF, or M-CSF, interleukins 1–7, particularly 1, 3, 6, and 7, TGF-$\alpha$ or $\beta$, erythropoietin, or the like, particularly human factors. Of particular interest is the presence of about 0.5–2, preferably 1, ng/ml G-MCSF, and 0.5–2, preferably 1 ng/ml, as well as a 0.1–2 U/ml/day of final concentration of erythropoietin, from about 100–300 ng/ml/day of G-CSF and about 1–10 ng/ml/day of stem cell growth factor (S-CSF, also referenced as Mast Cell Growth Factor or Kit ligand). It is understood that one or more, preferably at least two of the growth factors will be provided by secretion from transformed cells, which will be present in an amount sufficient to maintain the desired level of the growth factors in the perfusion medium.

Conveniently, in the reactor, physiologic temperature will be employed, namely 37° C., although lower temperatures may also be employed, including 33°, usually not being below 25° C. Humidity will generally be about 100%, where the air will contain about 5% carbon dioxide. The perfusion medium may be oxygenated external to the reactor or internal to the reactor, various means being provided for internal oxygenation. Internal oxygenation may be achieved with hollow fibers, porous sintered disks, silicone tubing or other membranes of suitable porosity and hydrophobicity. The nutrient level and metabolic product level will normally be maintained in a relatively narrow range. Glucose level will usually be in the range of about 5 to 20 mM, usually about 10 to 20 mM, lactate concentration will usually be maintained below about 35 mM and may be allowed to be over 20 mM. Glutamine concentration will generally be maintained in the range of about 1 to 3 mM, usually 1.5 to 2.5 mM, while ammonia concentration will usually be maintained below about 2.5 mM, preferably below about 2.0 mM.

The flow of fluid may be by gravity, by a pump, or other means, where the flow may be in any direction or a multiplicity of directions, depending upon the nature of the packing in the reactor. Desirably, laminar flow may be employed where the flow may be substantially horizontal across the reactor or vertical flow may be employed, where the flow is from the bottom to the top of the reactor or vice-versa.

Where the source of human hematopoietic cells is suspected of having neoplastic cells, e.g., leukemic lymphoma or carcinoma, the perfusion flow can be selected so as to segregate the normal progenitor cells from the neoplastic hematopoietic cells. It is found that normal hematopoietic progenitor cells adhere to stroma and matrix proteins with an affinity able to withstand approximately 1.5–2.0 dynes/cm$^2$ stress from longitudinal fluid flow. By contrast, neoplastic cells and their progenitors have a substantially weaker affinity for stroma, in the range of about 0.05–1.2 dynes/cm$^2$. By providing for a perfusion flow rate which provides sheer stress rates intermediate between that tolerated by normal and neoplastic progenitor cells, generally greater than 1 dyne/cm$^2$, one can provide for separation of the neoplastic progenitor cells from the normal progenitor cells, generally maintaining the perfusion for at least about two days, preferably at least about five days, and more preferably seven days or more. In this manner, one can expand normal hematopoietic cells from a human patient, while at the same time using the appropriate flow rates, separate neoplastic cells. In this manner, one can provide for autologous hematopoietic cells from a patient suffering from neoplasia, expand the normal hematopoietic cells during a period of treatment of the patient by chemotherapy or X-irradiation, and then restore normal hematopoietic cells to the patient to restore hematopoiesis and the immune system of the patient.

Illustrative of the use of shear stress to separate hematopoietic tumor cells from normal hematopoietic cells is the situation of chronic myelogenous leukemia (CML). Shear stress tolerance for CML cells is in the range of 0.05–1.2 dyne/cm$^2$. This difference permits the efficient removal of CML cells with an individual bone marrow sample. By employing a shear rate of about 1.2–1.5, preferably 1.3, dynes/cm$^2$, the CML cell may be efficiently separated.

The shear stress tolerance within an individual's bone marrow cells may be determined using a tapered radial flow chamber. In the radial flow chamber, the shear stress experienced by the cell decreases with distance "d" from the start of the chamber as a function of 1/d. Bands may then be analyzed for cell population and the shear stress set for the desired cell population to be retained.

For the removal of leukemic stem cells, progenitor cells and stem cells from bone marrow samples from patients with leukemia are first placed into a radial flow chamber. The radial flow chamber consists of two parallel plates, made of polycarbonate or glass, which permit the adhesion of bone marrow stromal cells to the lower plates. The initial measurements can be performed by either (1) establishing a preformed confluent monolayer of bone marrow stromal cells prior to hematopoietic cell infusion and then initiating fluid flow after 12–24 hours, or (2) inoculating the patient's bone marrow directly into the flow chamber without using a preformed stromal monolayer, and then waiting 3–4 days before establishing the fluid flow, usually 0.05–1.0 cc/min. The plates are sealed together at the edges through a rubber gasket, and held together with adjustable screws. At the narrow, infusion, end of the chamber a tube brings fluid into the chamber from a reservoir delivered by a constant pressure syringe-type pump. At the wide, collection end, the fluid and removed cells are collected through a separate tube (see FIGS. 3 and 3b). After the period of perfusion (usually 3–7 days), the nonadherent cells are removed, and the plates are separated, cells from each of 3–5 regions are separately removed by aspiration and rubber policeman, and each fraction is analyzed for the presence of leukemic cells by standard techniques (usually karyotypic analysis by chromosomal banding). Comparison of the leukemic analyses of each fraction demonstrates in which fraction (i.e. at which shear stress), the leukemic cells fail to adhere to the stroma and are removed. In these chambers, the shear stress perceived by the cells declines exponentially as a function of the distance are from the inlet. (See FIG. 3c). Typically, the nonadherent cells are all or nearly all leukemic, whereas cells adhering at the in the narrowest ½ of the chamber are all or nearly all normal.

Based upon the results of these measurements, a series of parallel, rectangular chambers is established in which the rate of fluid flow (see FIGS. 4a and 4b) over the lower surface creates a shear stress rate which was found in the tapered chamber to remove leukemic cells from the stroma without removing all of the normal cells. In the case of chronic myelogenous leukemia patient bone marrows, this shear stress is typically 0.01–0.05 dynes/square cm. The actual flow rate employed will depend on the size and geometry of the chambers. Bone marrow cells from the patient will be cultured in these rectangular chambers at a concentration of $5 \times 10^6$/ml to $50 \times 10^6$/ml in Iscove's Modified Dulbecco's Medium with 5–20% (typically 10%) Fetal calf serum plus 0–15% (typically 10%) horse serum, with or without $10^{-6}$M hydrocortisone. The bone marrow cells will be cultured for 12–24 hours without fluid flow, and then fluid flow will be initiated. The cells will be cultured for 3–7 days, at which time all of the nonadherent cells will be discarded. The adherent cells will be recovered from the rectangular plates by aspiration and mechanical agitation, and then collected. These cells can then be either directly returned to the patient, or stored in liquid nitrogen by standard techniques for later use.

Cells other than those of the hematopoietic system also may be separated using differential tolerance to shear stress. Thus, where there are distinct subpopulations of cells within a complex mixture of cells the methods described above can be used to separate out a cell type of interest from within a suspension of cells derived from, e.g. skin, liver, muscle, nerve, or epithelium. Of particular interest is the separation of tumor cells from within a population of normal cells. The population of cells to be separated will be contacted with a suitable stromal substrate as described below, such as a purified protein or cellular component to which the cells of interest adhere. The shear stress tolerance for each of the adherent subpopulations is determined as described above. The fluid flow can then be adjusted appropriately so as to retain the desired subpopulation of cells on the stroma. The desired cells are then collected as described above.

A variety of packings may be used in the reactor to provide for adherent growth of the cells, while maintaining some physical separation between the stromal cells and the hematopoietic cells, and while allowing for some contact or close juxtaposition between the stromal cells and the hematopoietic cells. In this way, the factors secreted by the stromal cells may be readily taken up by the hematopoietic cells to encourage their proliferation and, as appropriate, differentiation and maturation.

The protein matrix to support the cells may take the form of shredded collagen particles, e.g., sponges or porous collagen beads, sponges or beads composed of extra-cellular bone matrix protein from bone marrow, or protein coated membranes, where the protein may be collagen, fibronectin, hemonectin, RGDS peptide, mixed bone marrow matrix protein, or the like. Pore sizes of membranes will generally range from about 1 to 5μ to allow for interaction between the different cell types, while still retaining physical separation.

Membranes may be employed, which will be protein coated. Various membrane materials may be employed such as polypropylene, polyethylene, polycarbonate, polysulfonate, etc. Various proteins may be employed, particularly collagen or the other proteins which were indicated previously. The membrane should have sufficiently small pores, that the transformed cells may not pass through the membranes, but may grow and form a confluent layer on one side of the membrane and extend portions of the cell membrane into the pores. Generally the pores will be in the range of about 1 to 5μ. In this manner, the hematopoietic stem cells may grow on the opposite side of the membrane and interact with the transformed cells, whereby factors may be transferred directly from the transformed cells to the hematopoietic progenitor cells and the progenitor cells, the stem cells are able to attach to the intruded cytoplasmic projections which have passed into the pores. Hematopoietic differentiation from the stem cells occurs on one side of the membrane and differentiated progeny are unable to squeeze back through the pores, which are already largely occupied by cytoplasmic projections from the fibroblasts. As hematopoietic cells mature and differentiate, they will be released from the membrane into the nutrient medium.

The reactor may be packed with the various particles in a central portion of the reactor to define a central chamber, which will be separated from an upper chamber and a lower chamber. Alternatively, one or a plurality of membranes may be introduced, where two membranes will define a region associated with either the stromal cells or the hematopoietic cells, where the regions will alternate between stromal and hematopoietic cells. In this way, one may provide for differential perfusion rates between the chambers of the hematopoietic cells and the stromal cells. The medium exchange rate will generally fall within the ranges indicated above.

Instead of or in addition to contact between hematopoietic cells and stromal cells, one may provide for stromal cells in an environment where the two types of cells are inhibited from any contact. Thus, the stromal cells would provide for the various factors to support the growth of the hematopoietic cells and the stromal cell conditioned medium used for perfusion of the hematopoietic cells. For example, one could use two hollow-fiber cartridges in series, where the first cartridge would contain stromal cells under conditions which allow for the continued growth of stromal cells, while a second cartridge would contain the hematopoietic cells which would be perfused with the conditioned medium.

Furthermore, it is desirable to provide for continuous stromal cell proliferation as a source of growth factors. In order to maintain continuous stromal cell proliferation, it is desirable to initially employ stromal cells at a subconfluent stage. Various techniques may be employed to provide for replacement of the stromal cell layer when confluence is approached or reached. For example, one could provide for a plurality of chambers in which stromal cells may grow and the hematopoietic cells may be moved in accordance with the chamber which has the stromal cells at a subconfluent level. Thus, by having a movable barrier between the chambers, when the stromal cells approach confluence, generally after about 8–12 weeks, one could open or remove the barrier between the chambers and allow for the stromal cells to migrate into the new chamber and allow for the hematopoietic cells to come in contact with the subconfluent stromal cells, while the subconfluent stromal cells feed the factors to the chamber comprising the hematopoietic cells (FIG. 5a and FIG. 5b). The transfer of the hematopoietic cells can be achieved by appropriate flow rates or by other convenient means. One can provide for various wells in the chamber, which are divided by appropriate walls, after seeding in one well, when the cells become confluent, cells will then move over into the next well and seed the next well in a subconfluent manner. Another modification of the system is one in which, after 8–12 weeks in culture, the hematopoietic cells are exposed to new, proliferating stromal cells. This is accomplished in one of several ways. This exposure to proliferating stromal cells is accomplished in one of several ways. In the first technique, the culture are exposed to EDTA for 3–5 minutes, which removes the hematopoietic stem cells from the stromal cells. The removed cells are then transferred to a new culture vessel, which may itself contain bone marrow stromal cells seeded 3–7 days prior. This process is repeated every 8–12 weeks. Another alternative approach is to add additional surface area by increasing the volume of the cultures and adding additional collagen beads to the cultures at 8–12 weeks. Finally, small organic molecules or proteins, particularly hormones, such as platelet-derived growth factor (at 100–500 ng/ml), interleukin 1 alpha, tumor necrosis factor alpha, or basic fibroblast growth factor or other molecules mitogenic to fibroblasts, can be added to the cultures every 3–7 days. This exposure to stromal mitogenic stimulatory factors promotes the continued proliferation of bone marrow stromal cells, and their continued production of hematopoietic growth factors. Thus, one can provide for the continuous subconfluent stage of the stromal cells.

Continuous fluid flow can also be used to selectively separate normal from cancerous cells within a bone marrow population. In this approach, a radial flow chamber is first used to determine the specific stromal adhesive properties of normal versus cancerous cells, and then a rectangular flow chamber with flow rates established to achieve a shear stress sufficient to remove the cancerous cells is used to preoperatively separate the normal and cancerous cells.

The subject method and apparatus also provides for the opportunity to recycle stem cells which are lost by the flow of the perfusion medium. The surface membrane protein marker CD34 substantially separates immature hematopoietic cells from mature hematopoietic cells. Thus, by capturing and recycling those cells which are CD34+, one may avoid the loss of stem cells to the medium.

Various techniques may be employed for capturing and returning the immature fraction of cells to the reactor. For example, one could label the cells with an antibody specific for CD34 and then use antibodies to the antibody for collecting the CD34+ cells and recycling them to the reactor. Alternatively to positive selection, one may use negative selection, whereby one would remove the mature cells employing antibodies to various markers associated with mature cells, such as antibodies to glycophorin A, CD33, MO1, OKT3, OKT4, OKT8, OKT11, OKT16, OKM1, OKM5 Leu7, Leu9, Leu M1, Leu M3, and the like. Various antibodies are available for markers specific for mature cells of the various hematopoietic lineages, lymphoid, myeloid and erythroid, and these antibodies may be used to remove the mature cells from the effluent from the reactor, followed by harvesting of the remaining cells and restoring them to the reactor. In this way, one can avoid forced decline in the cultures due to loss of stem cells and maintain unlimited stem survival in vitro.

Separation using antibody markers can be achieved in various ways, using standard techniques, individually or in combination, such as panning, fluorescence activated cell sorting, antibodies bound to various surfaces, e.g. polystyrene surface, metal microspheres and magnets, and the like. The antibodies are bound to a surface which allows for separation between adherent and non-adherent cells or the antibodies are labeled, directly or indirectly, which permits selection between labeled and unlabeled cells.

By following the subject procedures greatly extended periods of in vitro growth of hematopoietic cells may be achieved, generally providing ex vivo human hematopoiesis for at least six months in culture, with granulopoiesis being supported for at least four months and erythropoiesis for at least three months. In addition, hematopoietic progenitor cells are continuously generated throughout the culture resulting in net expansions of progenitor cells of over 10-fold from input cells.

In addition, by following the subject procedures greatly increased rates of stem cell division are supported, permitting the efficient insertion of retrovirally transfected genetic material. Genes inserted by the appropriate retroviral vector during an initial two week infection period can be expressed in up to 10–30% of all progenitor and precursor cells arising during subsequent culture for over four months in culture. These subject procedures thus support the successful transfer of genetic material into a highly proliferative human hematopoietic stem cell.

FIG. 1 is a schematic view of a perfusion chamber. Reactor 10 with cover plate 12 and floor plate 14 are joined by bolts 16, held in position by wing nuts 18. Three bolts are employed, so as to avoid warping. The chamber 20 has three sections, the middle section 22 containing the support matrix for the stromal cells, the bed of stromal cells, and the bone marrow cells. The central section 22 is separated from the top section 24 and the bottom section 26 by membranes or mesh 28 and 30 respectively. Conveniently, polysulfonate membrane may be employed or a stainless steel mesh, whose mesh size is small enough so that cells are contained within the central section of the chamber. The separating interphase may be placed in the chamber using an inner cylinder 27 which is sectioned to provide the separating membrane mechanical support. The top section 24 and the bottom section 26 need not be identical and will have tubing or membranes across which liquid media and gases are exchanged. The gases are exchanged across a hydrophobic, e.g., silicone, tube whose length (and thereby gas/liquid contact area) may be varied to allow for sufficient gas fluxes to support the needs of the cell population that is metabolizing in the central section. The media can be pumped or withdrawn directly from the top or bottom sections through port 32 and may be fed through delivery tube 34.

If desired, the top and bottom sections may be eliminated by using an external oxygenator. In this situation, the separating membrane is held in place under the glass cylinder 36 which fits into cylindrical groove plates 12 and 14 and the area inside of the cylindrical groove is indented to allow for good flow distribution across the membrane. This geometry allows the fluid from the finite number of inlet ports to mix and for radial pressure to equilibrate, leading to a uniform liquid flow across the separating membrane. This setup is suitable for chambers which have relatively few cells, so that oxygenation does not become limiting.

Figure 2:
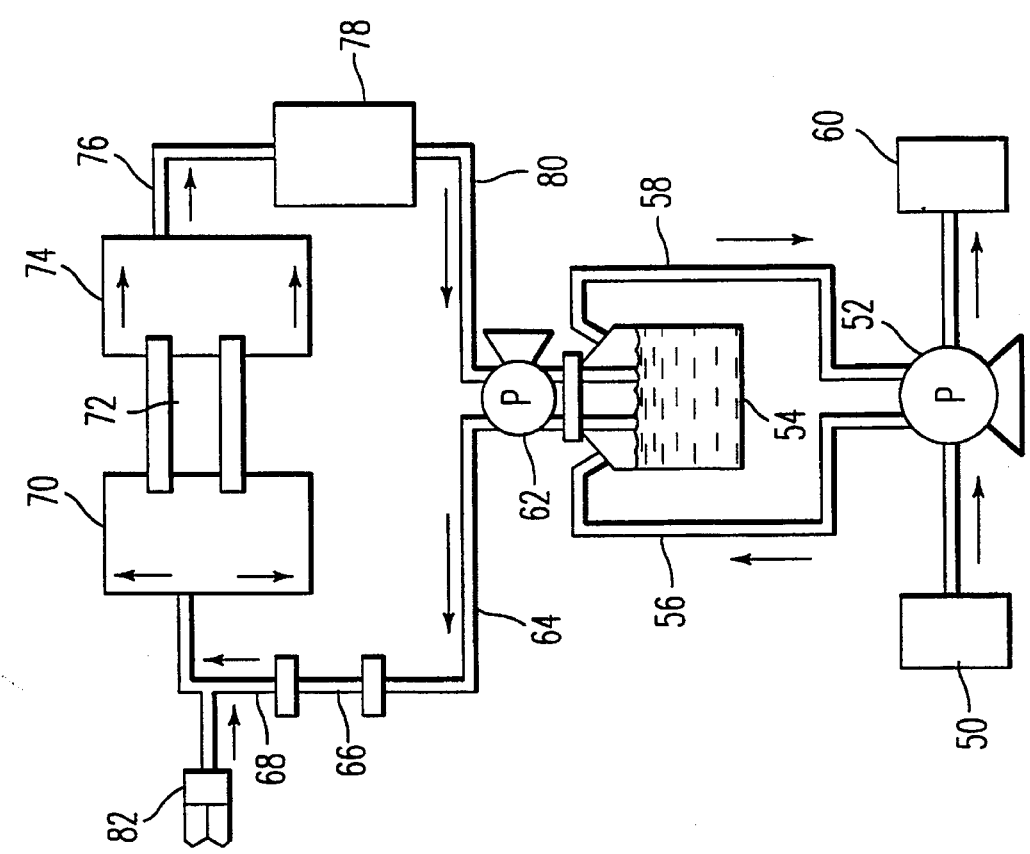
FIG. 2 is a schematic representation and flow diagram of the perfusion medium pathway.

In FIG. 2 is depicted a schematic representation of the loop that connects the perfusion chamber to the side media reservoir, oxygenator, sensor chamber, and sample/injection ports.

An external fresh media source 50 is pumped by means of pump 52 to a media reservoir through line 56 and spent media is withdrawn through line 58 from reservoir 54 by means of pump 52 to the spent media container 60 for further processing. A second pump 62 pumps media from the media reservoir 52 through line 64 through a hollow fiber oxygenator 66. The media is directed through line 68 to the first chamber of bioreactor 70. As appropriate, a means for injection of media component 82 is provided, for introducing the component into line 68 for transport by the media into the first chamber of bioreactor 70. The component may be test components, additional factors, or the like. The media from bioreactor 70 is directed through central chamber 72 into the second chamber 74 of the bioreactor. From there the media is directed by line 76 to in-line sensors 78 for detecting the change in composition of the media.

For example, it is desirable that the glutamine:glucose ratio be in the range of about 1:5-8, depending on the cell lines used; for instance, preferably 1:8 for transfected 3T3 cells. Furthermore, ammonium concentrations will preferably be below about 2.0 mM and lactate concentrations are preferably less than about 40 mM. By monitoring the effluent from the bioreactor, the media introduced into the bioreactor may be modified, oxygen partial pressure may be changed, gas flow rate may be altered, various components may be augmented, or the rate of perfusion may be slowed or increased.

From the sensors 78, the media is directed through line 80 by means of pump 62 to the reservoir 54.

By means of the flow path described above, the media in the side reservoir is slowly exchanged using a separate pump. This organization allows for separate control of the media exchange rate (the outer pump) and the flow rate through the oxygenator and perfusion chamber. The former is used to control the longer term change in the media composition and perfusion, while the latter may be used to control the dissolved oxygen tension and flow patterns in the chamber. The use of a small mesh biocompatible membrane allows for plug (piston) flow in the chamber and thus allows the precise control of delivery of growth factors and other special compounds that one may wish to introduce to the hematopoietic cells and stromal cells in very precise amounts.

After autoclaving the chamber and components of the loop, the reactor is assembled in a sterile environment. The media may be circulated through the side loop and chamber for a few days while signs of contamination are monitored. If sterile assembly is accomplished, the central section of the chamber is inoculated with either the extra-cellular matrix alone or a pre-inoculated extra-cellular matrix support that contains the stromal cells. The stromal cells are then either: (1) kept in the chamber for a period of a few days while their metabolic performance and/or growth factor responsiveness is monitored and if results are satisfactory, the bone marrow is inoculated; or (2) immediately seeded with bone marrow.

In either case, the cell layer is kept at the bottom of the central section of the perfusion chamber. The cells lay down additional extra-cellular matrix and the cell layer adheres to the separating membrane. At this time, the chamber may be inverted and the cell layer may then be located at the ceiling of the central section. In this configuration, the maturing cells will settle on the bottom of the central chamber as they lose their adherence to the stromal layer. This feature is important to prevent the damage caused by mature cells to the stromal layer and/or the less mature hematopoietic cells. This feature also makes the continuous removal of mature cells easier.

These cells are harvested by withdrawing the cells by syringe, or by continuously allowing the cells to flow out of the chamber, by the pressure of the perfused medium, through the exit tubing.

The stromal cells will, for the most part, be fibroblasts transformed with one or more genes providing for desired hematopoietic growth factors. The same or different cells may be transfected with the genes, depending upon the particular selection of host cells, the same or different cells may be used for a plurality of genes.

A wide variety of normal cells or stable lines may be employed. However, it is found that not all cell strains are permissible, since transformation of some cell lines may result in the overgrowth of the cells. Desirably, the cells which are employed will not be neoplastic, but rather require adherence to a support. The mammalian cells need not be human, nor even primate. A variety of nontransformed cells may be included in the adherent cell layer as well, including normal human bone marrow adherent cells, normal human spleen adherent cells, and normal human thymic epithelium.

Methods for transforming mammalian cells, including fibroblasts, are well known and there is an extensive literature of which only a few references have been previously given. The constructs may employ the naturally occurring transcriptional initiation regulatory region, comprising the promoter and, as appropriate the enhancer, or a different transcriptional initiation region may be involved, which may be inducible or constitutive.

A large number of transcriptional initiation regions are available which are inducible or constitutive, may be associated with a naturally occurring enhancer, or an enhancer may be provided, may be induced only in a particular cell type, or may be functional in a plurality or all cell types. The transcriptional initiation region may be derived from a virus, a naturally occurring gene, may be synthesized, or combinations thereof.

Promoters which are available and have found use include the chromosomal promoters, such as the mouse or human metallothionein-I or II promoters, actin promoter, etc., or viral promoters, such as SV40 early gene promoters, CMV promoter, adenovirus promoters, promoters associated with LTRs of retroviruses, etc. These promoters are available and may be readily inserted into appropriate vectors which comprise polylinkers for insertion of the transcriptional initiation region as well as the gene of interest. In other instances, expression vectors are available which provide for a polylinker between a transcriptional initiation region and a transcriptional termination region, also providing for the various signals associated with the processing of the messenger for translation, i.e., the cap site and the polyadenylation signal. The construction of the expression cassette comprising the regulatory regions and the structural gene may employ one or more of restriction enzymes, adaptors, polylinkers, in vitro mutagenesis, primer repair, resection, or the like.

The expression cassette will usually be part of a vector which will include a marker and one or more replication systems. The marker will allow for detection and/or selection of cells into which the expression cassette and marker have been introduced. Various markers may be employed, particularly markers which provide for resistance to a toxin, particularly an antibiotic. Preferably, gentamicin resistance is employed, which provides resistance to G418 for a mammalian cell host. The replication systems may comprise a prokaryotic replication system, which will allow for cloning during the various stages of bringing together the individual components of the expression cassette. The other replication system may be used for maintenance of an episomal element in the host cell, although for the most part the replication system will be selected so as to allow for integration of the expression cassette into a chromosome of the host.

The introduction of the expression cassette into the host may employ any of the commonly employed techniques, including transformation with calcium precipitated DNA, transfection, infection, electroporation, ballistic particles, or the like. Once the host cells have been transformed, they may be amplified in an appropriate nutrient medium having a selective agent, to select for those cells which comprise the marker. Surviving cells may then be amplified and used.

Host cells which may be employed include African green monkey cell line CV1, mouse cells NIH-3T3, normal human bone marrow fibroblasts, human spleen fibroblasts, normal mouse bone marrow fibroblasts, and normal mouse spleen fibroblasts. It should be noted that in some instances, depending upon the choice of vector and cell line, the cells may become neoplastic. It is important that the resulting transformed cells be capable of adherence, whereby the transformed cells maintain binding to a support, such as protein sponges, protein coated membranes, or the like.

Once the vector for expressing the appropriate growth factors has been constructed, it may be used to transform the cells by any convenient means. The resulting transformed cells may then be used to seed the supports, which have already been described. These supports may be introduced into the reactor or may be present at the time of seeding in the reactor. The cells will be allowed to grow for sufficient time to ensure that the cells are viable and are capable of producing the desired growth factors.

The reactor may then be seeded as appropriate with the hematopoietic cells. The hematopoietic cells may include substantially pure stem cells, a mixture of hematopoietic cells substantially free of mature hematopoietic cells of one or more lineages, or a mixture comprising all or substantially all of the various lineages of the hematopoietic system, at various stages of their maturation.

The cells are allowed to grow with substantially continuous perfusion through the reactor and monitoring of the various nutrients and factors involved. For the most part, the primary factors will be provided by the stromal cells, so that a steady state concentration of growth factors will normally be achieved. Since conditioned supernatants are found to be effective in the growth of the hematopoietic cells, one can provide for a ratio of stromal cells to hematopoietic cells which will maintain the growth factor at a appropriate concentration level in the reactor.

Transfected stroma can provide for the introduction of genes into human stem cells. In mice, retroviral mediated gene transfer into stem cells is made possible by pretreating mice with 5-FU and then growing the harvested bone marrow cells in WEHI conditioned media, which contains IL-3 and GM-CSF (Lemischka *Cell* 45:917, 1986). The artificial stroma, grown with a retroviral packaging cell line secreting a retroviral vector of interest, may be used to efficiently introduce genes into human stem cells. For example, human T-cells could be made resistant to HIV infection by infecting stem cells with the retroviral vector containing an HIV antisense sequence under control of a CDC2 regulatory sequence (Greaves, *Cell* 56:979–986, 1989) which would allow for tissue specific expression in T-cells. There would be a factor provided by the retroviral packaging cell line essential for replication of the retrovirus; this factor would be absent in the hematopoietic target cells. Once the virus was transferred to the hematopoietic target cells, it would no longer be able to replicate.

Figure 3A:
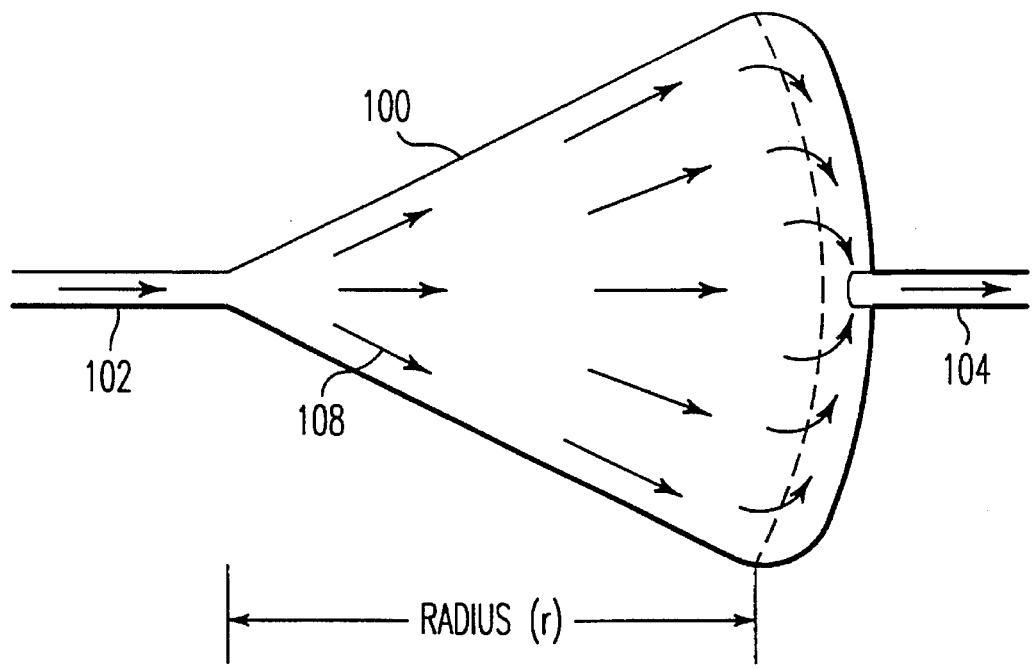
FIG. 3a is a schematic view of a flow chamber for measuring shear stress for separation of cells.
Figure 3B:
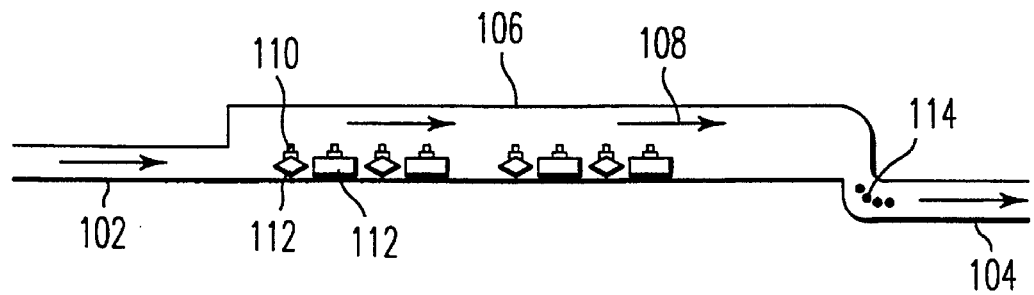
Figure 3C:
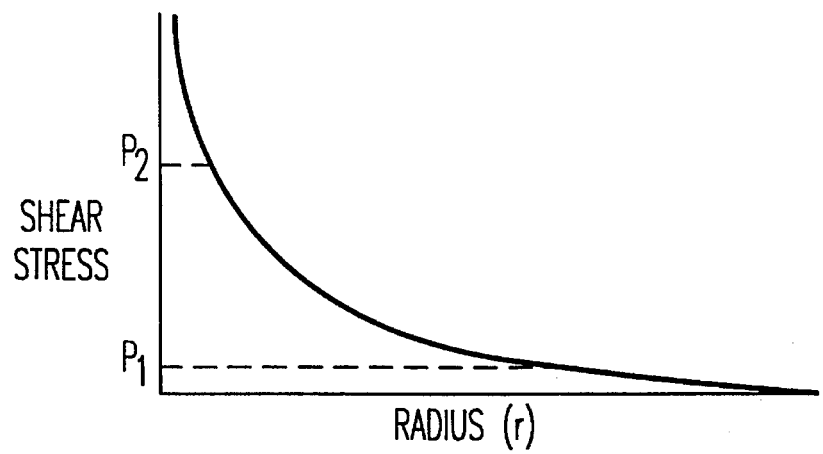
FIG. 3c is a graph of a shear stress profile for hematopoietic cells.

In FIGS. 3a and b are depicted radial flow chamber 100 having inlet 102 and outlet 104, and with chamber 106 where the arrows 108 indicate the direction of flow. Hematopoietic cells 110 are seeded onto a stromal layer 112 in the chamber and grown. The flow rate will determine which cells are able to adhere, the non-adherent cells 114 passing out through outlet 104.

Figure 4A:
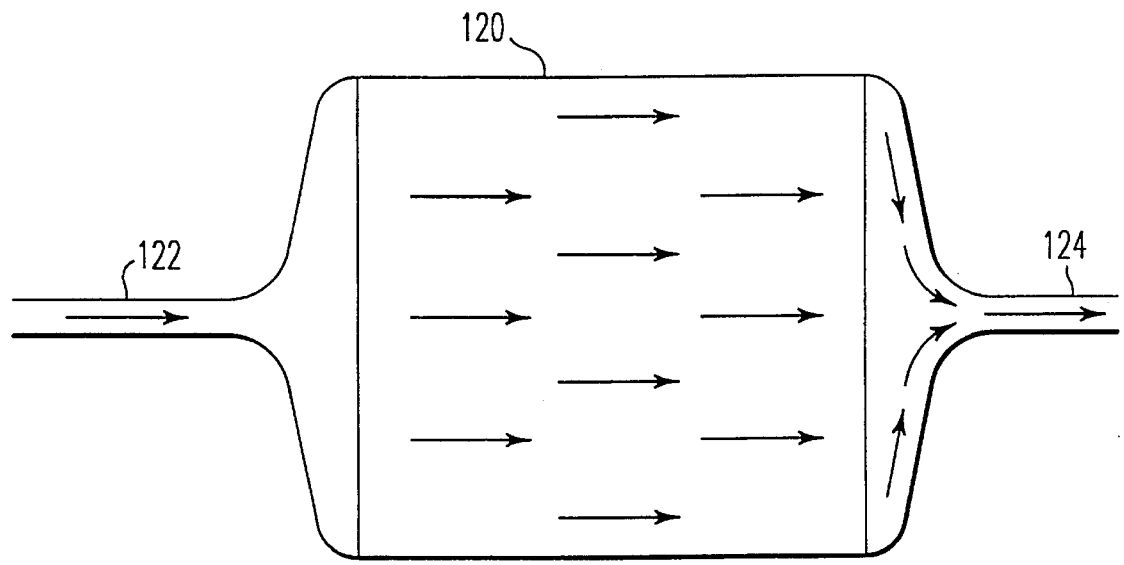
FIGS. 4a and 4b are top and side views of a flow chamber for growing and separating hematopoietic cells.
Figure 4B:
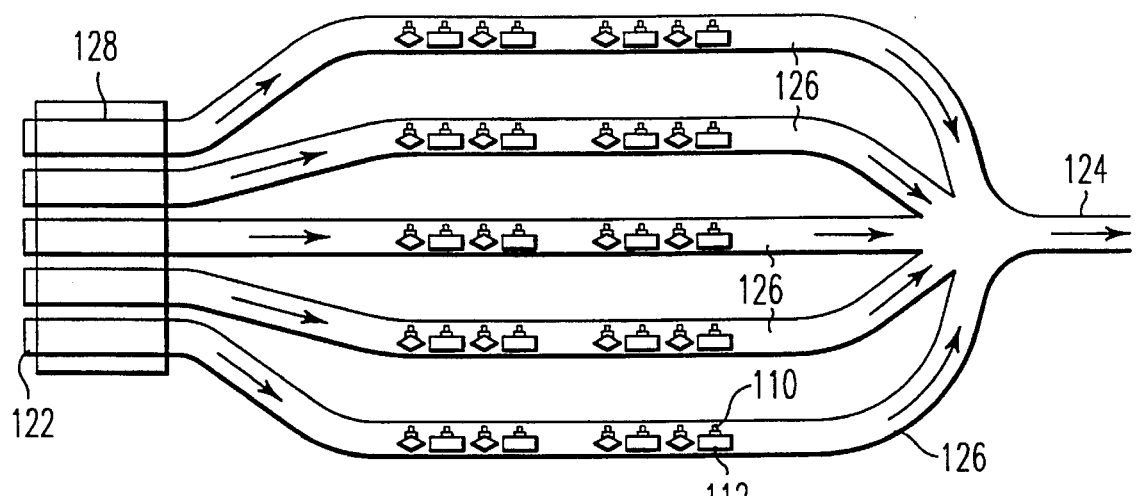

In FIGS. 4a and 4b, growth chamber 120 is provided having inlet 122 and outlet 124. In FIG. 4b, inlet 122 comprises a manifold 128 which feeds individual chambers 126 containing cells 110 and stroma 112 in the chamber 126 for growth and separation.

In FIGS. 5a and 5b are shown growth chambers in which barriers 134, 136, 138 are removed schematically during culture: barriers 134 at about week 8–10; barrier 136 at about week 18–20 and barrier 138, at about week 28–32.

The following examples are offered by way of illustration and not by way of limitation.

EXPERIMENTAL

I. Formation of Transformants

The growth factor human GM-CSF (Wong, *Science*, 228:810–815, (1985)) was inserted into a eukaryotic expression vector. The hGM-CSF cDNA (EcoRI to AhaIII, approximately 700 bp fragment) was cloned into an EcoRI to PstI fragment of pSP65. (Melton, *Nucl. Acids Res.* 2:7035–7056 (1984)). The resulting plasmid was pSP65GM-CSF. The mouse metallothionein promoter (Glanville, *Nature*, 292:267–269, (1981)) was digested with EcoRI and BglII and the approximately 2 kb fragment containing the promoter was inserted into the EcoRI to BamHI fragment of pSP65 to make p65MT. The plasmid pMT GM-CSF was then constructed by digesting pSP65GM-CSF with EcoRI, filling in the overhang with the Klenow fragment of DNA polymerase I and then digesting the resulting linearized DNA with HindIII to isolate the 700 bp fragment comprising the coding region of GM-CSF. This fragment was subcloned into the SalI filled/HindIII site of p65MT. The 2.7 kb fragment comprising the metallothionein promoter and the GM-CSF coding region was then isolated and placed into pSV2neo (Southern and Berg, *J. Mol. Appl. Genet* 1:327 (1982)) from which the SV-40 promoter was removed. This results in the SV-40 poly A signal downstream of the GM-CSF coding sequence.

The neomycin resistant gene, which confers resistance to the antibiotic gentamicin (G418) was taken from pSV2neo by isolating the approximately 3 kb PvuII to EcoRI fragment and placing EcoRI linkers onto the PvuII site. The neo resistance gene with EcoRI ends was subcloned into the EcoRI site of the GM-CSF expression plasmid to create the plasmid MTGM-CSFneo.

The plasmid MTGM-CSFneo alone and as a cotransfection with the plasmid (Yang, *Cell* 47:3–10, 1986) encoding the gibbon ape IL-3 gene under the control of the SV-40 promoter and poly A site, were transfected by electroporation of linearized DNA into the African green monkey cell line CV1 and the mouse cell line NIH 3T3 cells. Transformants were selected by selection in media containing 500 mg/ml of G418, isolated, and screened for production of GM-CSF or IL-3 by bioassay of supernatants using AML-193 cells (Adams, et al., *Leukemia* 3:314 (1989)). Several of the positive lines were then employed as stroma for human bone marrow cells in Dexter culture.

In addition, normal mouse bone marrow cells were transfected with the above plasmids using the calcium/phosphate method of Okayama (Chen, *Mol. Cell. Biol.* 7:2745–2752, 1987) and were found to efficiently express the introduced genes.

GM-CSF and IL-3 secretion by the transfected fibroblasts was investigated. Serum free 72 hour culture supernatants were obtained from the NIH-3T3 cells and assayed for hGF secretion by $^3H$ uptake on target cells inhibitable by neutralizing rabbit anti-GM-CSF or anti-IL-3 antibodies. Proliferation induced by 20 mg/ml GM-CSF was set as 100 units GM-CSF and that induced by 10 ng/ml IL-3 was set as 100 units IL-3. The co-transfected cells produced about 35 units/ml of GM-CSF and about 57 units/ml of IL-3.

II. Perfusion Chamber

The perfusion chamber is a glass cylinder with Delrin caps to allow for autoclaving without deformation and biocompatability. The caps have cylindrical groves into which the glass cylinder fits. At the bottom of the grove an O-ring is placed to seal the lumen of the chamber. The caps have several holes into which Luer (Luer Lok) fittings are provided into which media and gas delivery lines are put as well as an extended tube into the central section of the chamber to sample adherent and/or non-adherent cells. The caps are attached with three long bolts, spaced 120°, placed outside the glass cylinder; wing nuts and washers are used to tighten the assembly.

The chamber is hooked to a side reservoir. The loop contains a pump, a chamber of on-line sensors, oxygenator, and sample and injection ports in addition to the side media reservoir. The media in the side reservoir is then slowly exchanged using a separate pump. This configuration allows for separate control of the media exchange rate and the flow rate through the oxygenator and perfusion chamber. The former is used to control the longer term change in the media composition and perfusion, while the latter may be used to control the dissolved oxygen tension and flow patterns in the chamber. The use of a small mesh polysulfonate membrane allows for plug flow in the chamber and the precise control of delivery of growth factors and other special compounds which one may wish to introduce into the bioreactor in very precise amounts.

The transfected stromal cells are seeded either over a bed of shredded collagen sponge or the stromal cells are placed on one side of a 5μ porous polycarbonate filter precoated with collagen and the stromal cells allowed to adhere to the filter over a number of hours. The cells are allowed to grow in an appropriate nutrient medium until the cells become confluent on one side while sending cytoplasmic projections through the pores. Bone marrow cells are then seeded on the other side of the membrane and the stem cells attach to the intruded cytoplasmic projections which have passed through the pores.

After autoclaving the chamber and components of the loop, the reactor is assembled in a sterile environment. The media is then circulated through the side loop and chamber for a few days while signs of contamination are monitored. The central section of the bioreactor is then inoculated with either the extracellular matrix alone or a pre-inoculated extracellular matrix support that contains the stromal cells. The stromal cells may then be kept in the chamber for a period of a few days while their metabolic performance and/or growth factor responsiveness is monitored and if results are satisfactory, the bone marrow is inoculated or immediately seeded with bone marrow. In either case, the cell layer is kept at the bottom of the central section of the perfusion chamber.

The cells lay down additional extra-cellular matrix and the cell layer adheres to the support. Where the membrane is used, the chamber may be inverted and the cell layer is then located at the ceiling of the central section. In this configuration, the maturing cells settle on the bottom of the central chamber as they loose their adherence to the stromal layer. The non-adherent cells are then harvested by constant cell flow, driven by the medium perfusion pressure, into the exit tubing.

In a typical run, the chamber was inoculated with NIH-3T3 cells on day one on shredded collagen sponge support. For the first 40 days perfusion rates and other operating variables were adjusted. At day 40 a reasonable steady state was achieved which was maintained for about 20 days. On day 64 the chamber was seeded with $33 \times 10^6$ human bone marrow cells. For the first 10 days the harvested cell count decreased until it settled in a steady state of about $7-8 \times 10^5$ cells produced every three days. Flow cytometric analysis showed that a constant fraction, about 20% of the harvested cells were HLA-DR positive. On day 90 a pump failure was experienced and the pH dropped below 6.9 overnight. When the perfusion rate was restored the production of non-adherent cells recovered and was approaching the previous steady state production rate when a bacterial contamination occurred. At this point, the study was terminated.

The above results demonstrated that a perfusion chamber is capable of performing ex vivo hematopoiesis, hematopoiesis may be restored ex vivo after a pH drop, the glucose concentration data showed that the hematopoietic cells grow primarily aerobically on glucose, since the glucose concentration drops after inoculation without increasing the lactate concentration indicating that oxygenation is limiting. The glucose/lactate (anaerobic) metabolism appears to be primarily due to the NIH-3T3 stromal bed. Similarly, the glutamine and ammonia concentrations reach pre-inoculum levels once the hematopoietic cell number levels off, implying that the glutamine consumption by the bone marrow cells is much less than that of the stromal bed.

III. Monitoring of Metabolic Products

The consumption and formation rates of glucose and lactate as well as glutamine and ammonia were determined for transfected NIH-3T3 cells. (The medium was IMDM plus 20% FCS). Increased glucose consumption was only observed for daily fed T-flasks, whereas all less frequently fed cultures follow the same slowly diminishing glucose uptake rate pattern. Cultures that were exchanged 50% daily were switched to the 100% daily exchange schedule on day 18, which resulted in an immediate increase in glucose consumption following the same trend as that observed for cultures exchanged 100% daily from day one. Lactate production rates follow a similar pattern, as the lactate yield on glucose is essentially a constant (0.9 lactate/glucose; indicating a largely anaerobic stromal metabolism).

The glutamine and ammonia concentrations show a pattern analogous to the glucose/lactate metabolism. Using values corrected for chemical decomposition of glutamine at 37° C., the glutamine consumption rate versus the glucose consumption rate shows relative uptake rates are constant, about 1:8 glutamine: glucose. The predicted optimum ratio varies with oxygen uptake rate—the ratio drops with increasing optimum uptake rate.

Analogous conclusions were supported by glucose/lactate metabolic data derived from normal bone marrow stromal fibroblasts. Under conditions of infrequent medium exchange the cultures were primarily anaerobic, with high steady state levels of lactate rapidly achieved and maintained. With more frequent medium exchange, the cell metabolism became more rapid, with increased glucose consumption and lactate production. No detectable consumption of glutamine was observed after correcting the data for spontaneous chemical decomposition. For both 3T3 cells and normal human bone marrow cells, the cells continue to divide and crowd when the serum/media exchange rate was above what appears to be a critical replacement schedule.

To further ascertain the relative importance of perfusion rate of serum versus that of nutrients, the following experiments were performed: (1) one set of T-flasks with 20% serum containing media exchanged daily; (2) two sets of T-flasks, one with 20% serum and the media exchanged every other day and one with 10% serum with the media exchanged daily; (3) two sets of T-flasks, one with 10% serum and the media exchanged every other day, one with 5% serum with the media exchanged daily; (4) two sets of T-flasks, one with 5% serum and the media exchanged every other day and one with 2.5% serum with the media exchanged daily. The serum exchange rate is the same within each group while the exchange rate of the nutrient containing media varies. The results from these experiments show that it is the exchange rate of the serum that is critical. While for the experiment (1) glucose consumption increased and by day four had substantially flattened out to a rate of about 9.5 mmoles/per day, in all of the other cases, the glucose consumption started below the original glucose consumption of Group I and dropped off in a substantially linear manner regardless of whether twice the amount of serum was used and changed every other day or half the amount of serum was used and the media changed every day. This supports the need for a critical perfusion rate of serum or one or more serum components that influence the metabolic growth behavior of the stromal cells.

It is evident from the above results, that one may grow hematopoietic cells in a bioreactor in an efficient manner. Stromal cells can be provided from homologous or heterologous sources, where the stromal cells have been transfected with genes to provide for the important growth factors. In this manner, serum need not be added to the media to support the growth of the cells. By providing for stromal cells which adhere to a support in a manner which allows for separation of hematopoietic cells from the stromal cells, the hematopoietic cells may be continuously harvested for use. By appropriate choice of combinations of growth factors, specific lineages of hematopoietic cells may be grown. In addition, if desired, the stromal cells may provide for a reservoir of transfecting viruses for the introduction of genes into the hematopoietic cells.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for obtaining ex vivo human stem cell proliferation, expansion, or both, comprising culturing human hematopoietic cells comprising human stem cells found in the human hematopoietic system in a substantially continuously perfused liquid culture medium in the presence of transformed stromal cells capable of excreting at least one growth factor which directs the proliferation, differentiation, or both, of said human stem cells, and thereby obtaining ex vivo proliferation, expansion, or both, of said human stem cells, while maintaining said culture under physiologically acceptable conditions.

2. The method of claim 1, further comprising harvesting human hematopoietic cells from said culture.

3. The method of claim 1, wherein said transformed stromal cells are transformed fibroblast cells.

4. The method of claim 1, wherein human hematopoietic progenitor cells are expanded in said culture.

5. The method of claim 1, wherein said stromal cells are adherent to a protein substrate.

6. The method of claim 1, wherein said stromal cells excrete a colony stimulating factor or an interleukin or both.

7. The method of claim 6, wherein said colony stimulating factor is human GM-CSF and said interleukin is human IL-3.

8. The method of claim 5, wherein said protein substrate is a protein coated membrane or protein sponge.

9. The method of claim 8, wherein said protein is collagen.

10. The method of claim 1, wherein said liquid culture medium comprises a glucose concentration in the range of about 5 to 20 mM, a glutamine concentration in the range of about 1 to 3 mM, a lactate concentration below about 35 mM, and an ammonia concentration below about 2.5 mM.

11. The method of claim 1, wherein said transformed stromal cells are separated from said human hematopoietic cells by a physical barrier.

12. The method of claim 2, wherein said transformed stromal cells are maintained at a subconfluent stage, prior to harvesting.

13. The method of claim 1, further comprising recycling human hematopoietic stem cells from said nutrient medium exiting said culture.

14. A method of growing human stem cells in culture, said method comprising:

inoculating a reactor vessel comprising, on a surface, heterologous stromal cells adherent to one side of a protein membrane with pores in a range of about 1–5 microns with human hematopoietic cells comprising human stem cells found in the human hematopoietic system, said inoculation being on the opposite side of said membrane from said stromal cells, wherein at least a portion of said stromal cells are transformed and capable of excreting a colony stimulating factor or an interleukin which directs the proliferation, differentiation, or both, of said human stem cells;

substantially continuously perfusing said cells in said reactor with a liquid culture medium comprising any additional growth factors necessary for proliferation, differentiation, or both, of said human hematopoietic cells, while maintaining said reactor under physiologically acceptable conditions, said cells being perfused at a rate providing ex vivo proliferation, differentiation, or both, of said human stem cells; and harvesting human hematopoietic cells from said reactor.

15. The method of claim 14 wherein said human hematopoietic cells are human bone marrow cells.

16. A method of growing human stem cells in culture, said method comprising:

inoculating a reactor vessel comprising, on a surface, stromal cells adherent to a protein substrate, with human hematopoietic cells comprising human stem cells found in the human hematopoietic system, wherein at least a portion of said stromal cells are transformed and capable of excreting at least one growth factor which directs the proliferation, differentiation, or both, of said human stem cells;

substantially continuously perfusing said cells in said reactor with a liquid culture medium comprising any additional growth factors necessary for proliferation, differentiation, or both, of said human stem cells, while maintaining said reactor under physiologically acceptable conditions, said cells being perfused either at a rate providing ex vivo division of said human stem cells or at a rate sufficient to maintain production of hematopoietic growth factors at about the endogenous level produced by said normal human bone marrow stromal cells; and harvesting human hematopoietic cells from said reactor, with the proviso that when said human hematopoietic cells inoculated into said reactor vessel are suspected of comprising neoplastic cells, said perfusing is at rate providing a force on said cells greater than the affinity of neoplastic cells to said stromal cells and less than the affinity of normal human hematopoietic cells to said stromal cells.

17. The method of claim 16, wherein said stromal cells excrete a colony stimulating factor or an interleukin or both.

18. The method of claim 16, wherein said at least one growth factor is human GM-CSF or IL-3.

19. The method of claim 16, wherein said perfusion rate results in a shear stress at the surface of the hematopoietic cells greater than about 1.0 dyne/cm$^2$.

20. The method of claim 16, wherein said protein substrate is a protein coated membrane or protein sponge.

21. The method of claim 20 wherein said protein is collagen, fibronectin, or both.

22. The method of claim 16, wherein said human hematopoietic cells are human bone marrow cells, and said perfusing is at a flow rate sufficient to maintain production of hematopoietic growth factors at about the endogenous level produced by said normal human bone marrow stromal cells.

23. A method of growing human hematopoietic cells in culture, said method comprising:

inoculating a reactor vessel comprising, on a surface, heterologous stromal cells adherent to one side of a protein substrate with pores in the range of about 1–5 microns with human hematopoietic cells comprising human progenitor cells found in the human hematopoietic system, said inoculation being on the opposite side of said membrane from said stromal cells, wherein at least a portion of said stromal cells are transformed fibroblast cells capable of adhering to a protein substrate and capable of excreting at least one growth factor which directs proliferation, differentiation, or both, of said human progenitor cells;

continuously or periodically perfusing said cells in said reactor with a liquid culture medium comprising any additional growth factors necessary for proliferation, differentiation, or both, of said human hematopoietic progenitor cells, while maintaining said reactor under physiologically acceptable conditions, said cells being perfused at a rate equal to a rate of from 50 to 100% daily liquid culture medium replacement for a cell density of from $1\times10^4$ to $1\times10^7$ cells per ml of culture; and harvesting hematopoietic cells from said reactor, with the proviso that when said human hematopoietic cells inoculated into said reactor vessel are suspected of comprising neoplastic cells, said perfusing is at a rate providing a force on said cells greater than the affinity of neoplastic cells to said stromal cells and less than the affinity of normal hematopoietic cells to said stromal cells.

24. The method of claim 23, wherein said human hematopoietic cells are human bone marrow cells.

25. The method of claim 23, wherein said liquid culture medium comprises a glucose concentration in the range of about 5 to 20 mM, a glutamine concentration in the range of about 1 to 3 mM, a lactate concentration below about 35 mM, and an ammonia concentration below about 2.5 mM.

26. A method for obtaining ex vivo human stem cell proliferation, expansion, or both comprising culturing human hematopoietic cells comprising human stem cells found in the human hematopoietic system in a liquid culture medium in the presence of transformed stromal cells capable of excreting at least one growth factor which directs the proliferation, differentiation, or both, of said human stem cells, wherein said liquid culture medium is replaced at a rate equal to 50 to 100% daily replacement for a cell density of from $1\times10^4$ to $1\times10^7$ cells per ml of culture.

27. The method of claim 14, wherein said liquid culture medium is replaced at a rate equal to 50 to 100% daily replacement for a cell density of from $1\times10^4$ to $1\times10^7$ cells per ml of culture.

28. The method of claim 16, wherein said liquid culture medium is replaced at a rate equal to 50 to 100% daily replacement for a cell density of from $1\times10^4$ to $1\times10^7$ cells per ml of culture.

29. The method of claim 1, wherein said liquid culture medium is replaced at a rate of 50 to 100% daily replacement.

30. The method of claim 14, wherein said liquid culture medium is replaced at a rate of 50 to 100% daily replacement.

31. The method of claim 16, wherein said liquid is replaced at a rate of 50 to 100% daily replacement.

32. The method of claim 23, comprising replacing said liquid culture medium at a rate of 50 to 100% daily replacement.

33. A method for obtaining ex vivo human progenitor cell proliferation, differentiation, or both, comprising culturing human hematopoietic cells comprising human progenitor cells found in the human hematopoietic system in a perfused liquid culture medium in the presence of transformed stromal cells capable of excreting at least one growth factor which directs the proliferation, differentiation, or both, of said human progenitor cells; wherein said cells are substantially continuously perfused by the liquid culture medium at a rate providing proliferation, differentiation, or both, of said ex vivo human progenitor cells while maintaining said culture under physiologically acceptable conditions.

34. The method of claim 33, wherein said liquid culture medium is replaced at a rate equal to 50 to 100% daily replacement for a cell density of from $1\times10^4$ to $1\times10^7$ cells per ml of culture.

35. The method of claim 33, wherein said liquid culture medium is replaced at a rate of 50 to 100% daily replacement.

36. The method of claim 33, further comprising harvesting human hematopoietic cells from said culture.

37. The method of claim 33, wherein said transformed stromal cells are transformed fibroblast cells.

38. The method of claim 33, wherein said stromal cells are adherent to a protein substrate.

39. The method of claim 33, wherein said stromal cells excrete a colony stimulating factor or an interleukin or both.

40. The method of claim 39, wherein said colony stimulating factor is human GM-CSF and said interleukin is human IL-3.

41. The method of claim 38, wherein said protein substrate is a protein coated membrane or protein sponge.

42. The method of claim 41, wherein said protein is collagen.

43. The method of claim 33, wherein said liquid culture medium comprises a glucose concentration in the range of about 5 to 20 mM, a glutamine concentration in the range of about 1 to 3 mM, a lactate concentration below about 35 mM, and an ammonia concentration below about 2.5 mM.

44. The method of claim 33, wherein said transformed stromal cells are separated from said human hematopoietic cells by a physical barrier.

45. The method of claim 36, wherein said transformed stromal cells are maintained at a subconfluent stage, prior to harvesting.

46. The method of claim 26, wherein said human hematopoietic cells are human bone marrow cells and human bone marrow stem cells are produced in said vessel; said method for the comprising transfecting said human bone marrow stem cells.

47. A method for obtaining ex vivo human progenitor cell proliferation, differentiation, or both, comprising culturing human hematopoietic cells comprising human progenitor cells found in the human hematopoietic system in a perfused liquid culture medium in the presence of transformed stromal cells capable of excreting at least one growth factor which directs the proliferation, differentiation, or both, of said human progenitor cells; wherein said cells are perfused by the liquid culture medium at a rate equal to a rate of from 50 to 100% daily media replacement for a cell density of from $1\times10^4$ to $1\times10^7$ cells per ml of culture, while maintaining said culture under physiologically acceptable conditions, and thereby obtaining ex vivo human progenitor cell expansion.

48. The method of claim 47 wherein said liquid culture medium is replaced at a rate of 50 to 100% daily replacement.

49. The method of claim 47, further comprising harvesting human hematopoietic cells from said culture.

50. The method of claim 47, wherein said transformed stromal cells are transformed fibroblast cells.

51. The method of claim 47, wherein said stromal cells are adherent to a protein substrate.

52. The method of claim 47, wherein said stromal cells excrete a colony stimulating factor or an interleukin or both.

53. The method of claim 52, wherein said colony stimulating factor is human GM-CSF and said interleukin is human IL-3.

54. The method of claim 51, wherein said protein substrate is a protein coated membrane or protein sponge.

55. The method of claim 54, wherein said protein is collagen.

56. The method of claim 47, wherein said liquid culture medium comprises a glucose concentration in the range of about 5 to 20 mM, a glutamine concentration in the range of about 1 to 3 mM, a lactate concentration below about 35 mM, and an ammonia concentration below about 2.5 mM.

57. The method of claim 47, wherein said transformed stromal cells are separated from said human hematopoietic cells by a physical barrier.

58. The method of claim 48, wherein said transformed stromal cells are maintained at a subconfluent stage, prior to harvesting.

59. The method of claim 47, further comprising returning to the culture human hematopoietic stem cells obtained from nutrient medium existing said culture.

60. The method of claim 47, wherein said human hematopoietic cells are bone marrow cells, and said perfusing with said liquid culture medium and said stromal cells support the division of human bone marrow stem cells, whereby human bone marrow stem cells are produced in said vessel; said method further comprising transfecting said human bone marrow stem cells.

61. A method for obtaining ex vivo human stem cell proliferation, expansion, or both, comprising culturing human hematopoietic cells comprising human stem cells found in the human hematopoietic system in a liquid culture medium which is replaced at a rate of at least 50% daily replacement in the presence of transformed stromal cells capable of excreting at least one growth factor which directs the proliferation, differentiation, or both, of said human stem cells, while maintaining said culture under physiologically acceptable conditions.

62. A method for obtaining ex vivo human stem cell proliferation, expansion, or both, comprising culturing human hematopoietic cells comprising human stem cells found in the human hematopoietic system in a liquid culture medium which is replaced at a rate of 50 to 100% daily replacement in the presence of transformed stromal cells capable of excreting at least one growth factor which directs the proliferation, differentiation, or both, of said human stem cells, while maintaining said culture under physiologically acceptable conditions.

63. The method of claim 61, wherein said human hematopoietic cells are bone marrow cells and human bone marrow stem cells are produced in said vessel; said method further comprising transfecting said human bone marrow stem cells.

64. The method of claim 61, further comprising returning to the culture human hematopoietic stem cells obtained said nutrient medium existing said culture.

* * * * *